United States Patent [19]
Altshuler et al.

[11] Patent Number: 6,080,146
[45] Date of Patent: Jun. 27, 2000

[54] METHOD AND APPARATUS FOR HAIR REMOVAL

[76] Inventors: Gregory Altshuler, 204 Broughton Dr., Beverly, Mass. 01915; Michael Smotrich, 62 Sunset Rock Rd., Andover, Mass. 01810

[21] Appl. No.: 09/028,416

[22] Filed: Feb. 24, 1998

[51] Int. Cl.[7] .................................................. A61B 18/18
[52] U.S. Cl. .................................. 606/9; 606/3; 606/12; 606/16
[58] Field of Search ................................ 606/9, 10, 11, 606/12, 3

[56] References Cited

U.S. PATENT DOCUMENTS

| | | | |
|---|---|---|---|
| 5,217,455 | 6/1993 | Tan | 606/9 |
| 5,226,907 | 7/1993 | Tankovich | 606/133 |
| 5,425,728 | 6/1995 | Tankovich | 609/9 |
| 5,595,568 | 1/1997 | Anderson et al. | 606/9 |
| 5,630,811 | 5/1997 | Miller | 606/9 |
| 5,647,886 | 7/1997 | Zaias et al. | 606/9 |
| 5,662,644 | 9/1997 | Swor | 606/9 |
| 5,669,916 | 9/1997 | Anderson et al. | 606/133 |
| 5,735,844 | 4/1998 | Anderson et al. | 606/9 |
| 5,752,948 | 5/1998 | Tankovich et al. | 606/9 |
| 5,766,214 | 6/1998 | Mehl, Sr. et al. | |
| 5,843,072 | 12/1998 | Furumoto et al. | 606/9 |
| 5,860,967 | 1/1999 | Zavislan et al. | 606/9 |
| 5,871,479 | 2/1999 | Furumoto et al. | 606/9 |
| 5,879,346 | 3/1999 | Waldman et al. | 606/9 |

FOREIGN PATENT DOCUMENTS

| | | |
|---|---|---|
| WO 9728752 | 8/1997 | WIPO . |
| WO 9738638 | 10/1997 | WIPO . |

*Primary Examiner*—Linda C. M. Dvorak
*Assistant Examiner*—Sonya Harris-Ogugua
*Attorney, Agent, or Firm*—Wolf, Greenfield & Sacks, P.C.

[57] ABSTRACT

A method and apparatus for the removal of, and at least inhibiting the regrowth of, unwanted hair by applying optical radiation to the follicle, including the hair shaft therein, of an energy, a duration and wavelength to enhance the optical absorption characteristics of at least some component, (i.e., melanosomes, tissue, etc.) of the follicle without appreciably damaging skin outside the follicle; and subsequently applying optical radiation to the follicle of a wavelength which is more readily absorbed by the components of the follicle having optical absorption characteristics enhanced during step (a) then by unenhanced components and of an energy and duration to heat such enhanced components sufficiently to substantially destroy the follicle. For preferred embodiments, melanosomes in the bulb of the follicle, and in other portions of the follicle are heated by the initial optical radiation sufficiently to at least partially darken such melanosomes by browning or carbonization, and such darkening also occurs in tissue surrounding the melanosomes. While a single pulse may be utilized to perform this function, it is preferably performed by a succession of pulses, with each successive pulse darkening additional components of the follicle. For one embodiment, this process is repeated until sufficient components of the follicle have been darkened so that the next pulse results in the substantial destruction of the follicle. Alternatively, the radiation for the second step may be either of a specific wavelength or a broad-band radiation which is more readily absorbed by the enhanced components than by unenhanced components, and of an energy and duration which is sufficient to result in the destruction of the follicle. Other variations on the basic technique are also possible.

24 Claims, 6 Drawing Sheets

BEFORE LIGHT IRRIDATION

AFTER FIRST LIGHT PULSE

AFTER SECOND LIGHT PULSE

AFTER THIRD LIGHT PULSE

METHOD AND APPARATUS FOR HAIR REMOVAL

FIELD OF THE INVENTION

This invention relates to methods and apparatus for both the removal of unwanted hair from a patient and the at least inhibiting regrowth thereof.

BACKGROUND OF THE INVENTION

Lasers, lamps and other sources of electromagnetic radiation are being increasingly utilized for the removal of unwanted hair, and for at least inhibiting, and in some instances preventing, the regrowth thereof, these techniques replacing techniques such as electrolysis and waxing previously utilized for hair epilation. Examples of such epilation techniques include U.S. Pat. Nos. 5,227,907 and 5,425,728 to Tankovich which involve applying a chromophore to the follicle and then applying radiation to the follicle of a wavelength selectively absorbed by the chromophore; U.S. Pat. No. 5,669,916 to R. Rox Anderson which involves epilation to remove the hair from the follicle, filling the empty follicle with a chromophore and then applying radiation to the follicle of a wavelength selectively absorbed by the chromophore to destroy the follicle; and U.S. Pat. No. 5,595,568 to R. Rox Anderson, et al. (the Anderson '568 patent) which involves applying energy of a wavelength preferentially absorbed by melanin in the follicle with sufficient energy and for a sufficient duration to destroy the follicle. However, while temporary hair removal can be achieved using the techniques indicated above at relatively low energy, for example 0.5 to 5 $J/cm^2$, much higher energy pulses are required in order to achieve permanent, or near permanent, hair removal. For example, to achieve this objective, pulse energies in the 30–40 $J/cm^2$ may be required.

However, such high energy levels present a number of potential problems. First, the spectial bandwidths normally utilized for most such hair removal techniques suggest the use of a ruby, alexandrite, diode or other laser. While such lasers are available which operate in the 30–40 $J/cm^2$ range and above, such lasers are generally far more expensive than comparable lasers operating at lower energy. This results in systems designed to achieve permanent hair removal using these techniques being far more expensive than if these results could be achieved using lower energy lasers.

Second, while the high energy lasers or other radiation sources are effective for destroying a hair follicle, they reach the follicle through the epidermis which also contains significant quantities of melanin, particularly in its lower portion adjacent the dermal/epidermal (D/E) junction, which is also sometimes referred to as the basal layer. Such high energy laser pulses passing through the epidermis can thus result in significant damage to the epidermis. The Anderson '568 patent deals with this problem by cooling the epidermis prior to and during the application of laser pulses thereto; however, this cooling adds to the cost of the required equipment. The high energy pulses are also potentially dangerous for a person's eyes or other parts of the body and must therefore be handled with great care, normally by a physician or other highly trained individual. Lower energy pulses would therefore be safer to use, possibly eliminating the cost involved in cooling the epidermis, and potentially permitting hair removal procedures to be performed by less skilled, and therefore less expensive, personnel.

Another desirable characteristic in performing hair removal procedures is to be able to perform the procedure as quickly as possible. For example, it is preferable that the hair on a given area of a patient's body be removed in a matter of minutes, as opposed to an hour or more. While the patient appreciates not being subjected to the procedure over long periods, reducing the time for the procedure is particularly advantageous to the operator who can improve both his own productivity and that of what can be a relatively expensive piece of equipment thereby enhancing the profitability of his business. However, as is discussed in greater detail later, the time required to cover a given area is inversely proportional to the fluence and directly proportional to power. Therefore, prior art systems requiring high fluence for permanent hair removal have either operated relatively slowly, thereby requiring long periods of time for removal of hair from large areas such as the legs, and/or have required a very high power, and thus very expensive, source. Therefore, for a given power source, reducing the required fluence from for example 30 $J/cm^2$ to 5 $J/cm^2$ could result in a six-fold reduction in the time required for a given procedure.

For the reasons indicated above, and others, a need exists for an improved technique for hair removal which provides long-term inhibition of hair regrowth and potentially permanent hair removal at fluences far below the 30–40 $J/cm^2$ of current techniques, and preferably at fluences in the 1–5 $J/cm^2$ range.

SUMMARY OF THE INVENTION

In accordance with the above, this invention provides a method and apparatus for the removal of, and for at least inhibiting the regrowth of, a patient's hair, the hair being in the form of a hair shaft growing from a hair follicle. Since, as will be discussed in greater detail later, particularly for the lower portions of the follicle there is a substantial joining of the hair shaft and follicle, the term "follicle" as used hereafter will frequently refer to both the hair shaft and follicle. The invention involves (a) applying optical radiation to the follicle of an energy, duration and wavelength to enhance the optical absorption characteristics of at least some components of the follicle without appreciably damaging skin outside the follicle, and (b) applying optical radiation to the follicle of a wavelength which is more readily absorbed by the components of the follicle which have had their optical absorption characteristics enhanced during step (a) above then unenhanced components, the energy and duration of the radiation applied during step (b) heating such components sufficiently to substantially destroy the follicle (including the hair shaft). For preferred embodiments, melanosomes in the follicle are heated sufficiently during step (a) to darken the melanosomes, preferably by at least partially browning or carbonizing such melanosomes. Tissue surrounding such melanosomes may also be carbonized and/or water in such tissue may be evaporated, resulting in the bubbles surrounding the darkened melanosomes. More generally, the bubbles form in the bulb and other areas of the follicle containing melanosomes. The vaporization of water from the follicle tissues makes it easier for such tissue to be carbonized and/or destroyed during subsequent occurrences of step (a) and/or during step (b), while the bubbles surrounding the follicle hold heat therein to accelerate the carbonization/browning or other darkening process of the follicle, while protecting surrounding tissue from damage.

In practicing the invention, the wavelength of the optical radiation applied to the follicle during step (a) should be one preferentially absorbed by melanosomes, for example a wavelength in the 600–1100 nm range, with a wavelength in the 650–800 nm range being preferred. Similarly, the wavelength applied during step (b) should be a wavelength which is absorbed by carbon, but is not preferentially absorbed by melanosomes, and which is also not preferentially absorbed by blood. A wavelength of 800 nm–1300 nm might be used during this operation, or a broader band signal might be used. In the former case, one option is Na: Yag laser operating at approximately 1060 nm, while in the latter case, an incandescent light source might be used having radiation across a broad spectrum, or lamps such as a mercury arc lamp, halogen lamp or fluorescent lamp may be used having lines at various points along the spectrum.

The optical radiation applied during step (a) may be in the form of a single pulse or multiple pulses, with each pulse for example having energy sufficient to carbonize melanosomes in the follicle, but preferably not sufficient to substantially carbonize epidermal melanosomes.

Where multiple pulses are used during step (a), each successive pulse changes the optical characteristics of additional melanosomes, tissue, or other components (hereinafter sometimes referred to as "components") of the follicle. In particular, where multiple pulses are utilized, each pulse may heat and carbonize, brown or otherwise alter/enhance the optical characteristics of components of the follicle, such changed components formed during one pulse absorbing optical radiation of each successive pulse to heat and alter the optical characteristics of additional components of the follicle. For one embodiment of the invention, this process can continue until sufficient components in the follicle have had their optical characteristics changed so that the next successive pulse functions as step (b) optical radiation to destroy the follicle. Alternatively, step (b) radiation may have significantly greater energy than that of step (a) and/or steps (a) and (b) may be at different wavelengths. In this case, the higher energy step (b) pulse could be at a wavelength which is not preferentially absorbed by melanosomes or blood so as not to cause significant tissue heating, but to for example be absorbed by and to thus heat the browned or carbonized components of the follicle, the pulse being of sufficient energy to destroy such components and thus the follicle.

It is also possible for the optical radiation for step (a) and step (b) to be from the same pulse at the same wavelength, the pulse being in the form of a narrow spike functioning as a step (a) optical radiation and an extended porch or plateau as the step (b) optical radiation.

The invention can also provide an apparatus for epilation of hair which apparatus includes a source of radiation having a wavelength in the 600–1100 nm range, and means for applying a pulse of the radiation from the source to an area of the skin containing hairs to be epilated. The pulse is of an energy and duration to cause heating of melanosomes in the hair follicle sufficient to change the optical absorption characteristics of such melanosomes by darkening the melanosomes through browning, carbonization or the like, and to do the same to tissue surrounding such melanosomes. Such pulse should not however be of sufficient energy to destroy the follicle. The means for applying is repetitively operative to apply successive pulses of the radiation to the area, each successive pulse heating both the melanosomes and the carbonized tissue, resulting in further tissue carbonization in the follicle; the number of such pulses applied by the means for applying to the area of the skin being treated being sufficient to result in the destruction of the follicle. The source may be a continuous wave source, with the means for applying passing over the area a plurality of times, each pass resulting in a pulse being applied to the area. In such case, the hairs to be epilated may be in a plurality of adjacent areas, the means for applying making a plurality of passes over such areas, with the areas being passed over in succession during each pass. Alternatively, the source may be a pulsed source.

The foregoing and other objects, features and advantages of the invention will be apparent from the following more particular description of preferred embodiments of the invention as illustrated in the accompanying drawings.

IN THE DRAWINGS

DETAILED DESCRIPTION

Figure 1:
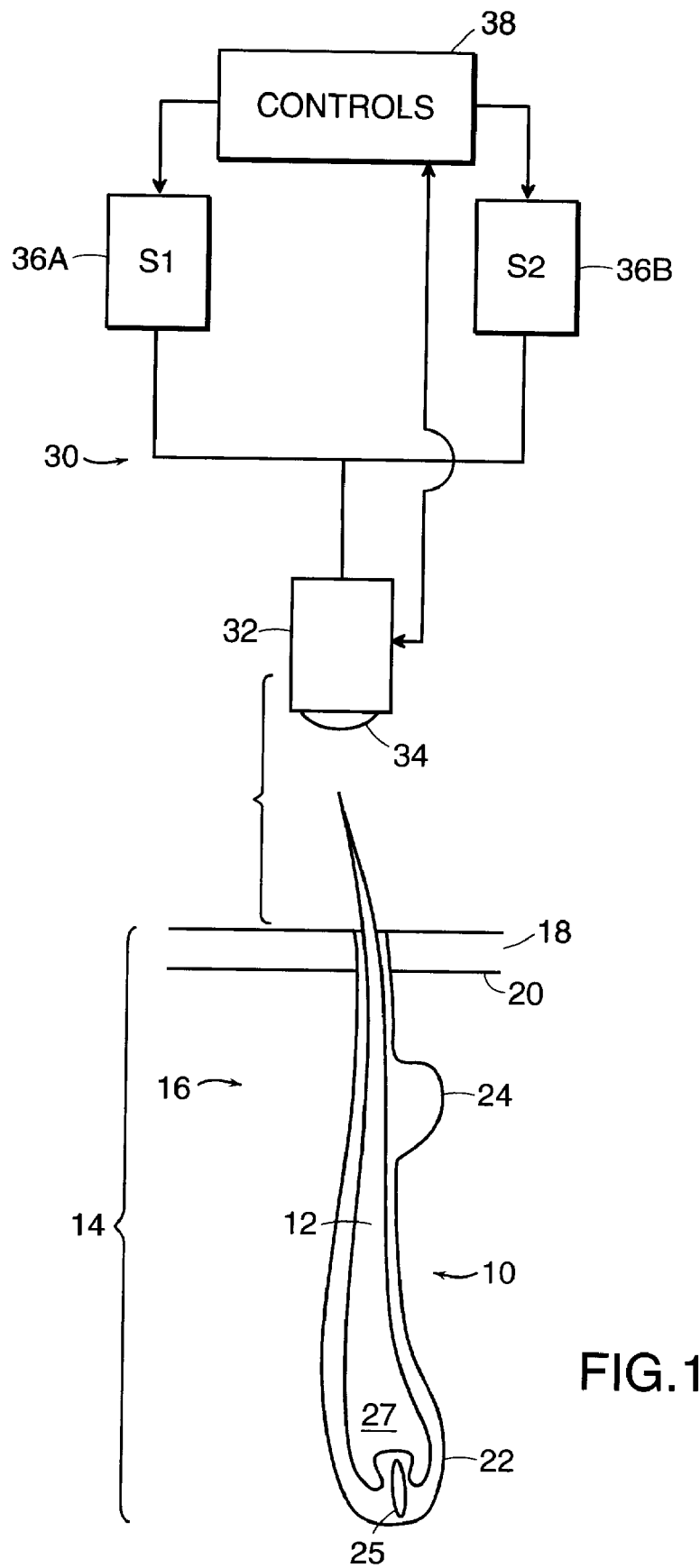
FIG. 1 is a schematic representation of a single hair follicle and of apparatus for use therewith in practicing the teachings of this invention.

FIG. 1 illustrates a hair follicle 10 having a hair shaft 12 growing therefrom and extending above the level of the patient's skin 14. The patient's skin includes a dermis 16 covered by an epidermal layer 18, the junction 20 between these two being referred to hereinafter as the dermal-epidermal (DE) junction or basal layer. The follicle, which extends approximately 3–4 mm into dermal layer 16 has a bulb 22 at its lower or distal end and a bulge 24 approximately 1–2 mm into the dermis. Bulb 22 includes the dermal papilla 25 and matrix cells 27 at the distal end of the hair shaft which contain significant quantities of melanosomes, with lesser quantities of melanosomes also being present in other areas of the follicle (including the hair shaft). The quantity of melanosomes in the follicle in general, and in matrix 27 and the remainder of hair shaft 12 in particular, depends on the color of hair shaft 12, dark hair being higher in melanosomes than light hair (i.e., blonde or gray).

Apparatus 30 includes an applicator 32 having a surface 34 from which optical radiation is emitted, sources of optical radiation 36A and 36B and controls 38. While applicator 32 may be spaced from the patient's skin as shown in FIG. 1, for preferred embodiments, hair shaft 12 is shaved so as to not project above the skin and surface 34 of applicator 32 is in contact with the skin. If the applicator is being utilized to cool the epidermis, as taught in the Anderson '568 patent, then it is preferable that surface 34 be in pressure contact with the skin to assure good thermal contact. However, this invention may be practiced with the applicator either in contact with the skin or spaced therefrom and, as will be discussed later, cooling of the skin may not be required.

Sources 36A, 36B may be diode, ruby, alexandrite, Na:Yag or other suitable lasers or may be other suitable radiation sources such as an incandescent lamp, mercury lamp, halogen lamp, fluorescent lamp, flash lamp, or the like. As will be discussed later, the sun or other ambient light source may in some instances by used in lieu of source 36B, and for at least some embodiments, only one source 36 is required. Controls 38 may be a suitably programmed microprocessor or other general purpose computer, may be a special purpose computer designed to perform the function, or may be a hybrid combination of hardware and software. Controls 38 may receive information from applicator 32 and possibly from sources 36 and may use the inputs thereto and other information to control the operation of the sources and, to the extent necessary, applicator 32 in accordance with the teachings of this invention as described hereinafter.

Operation

Figure 2:
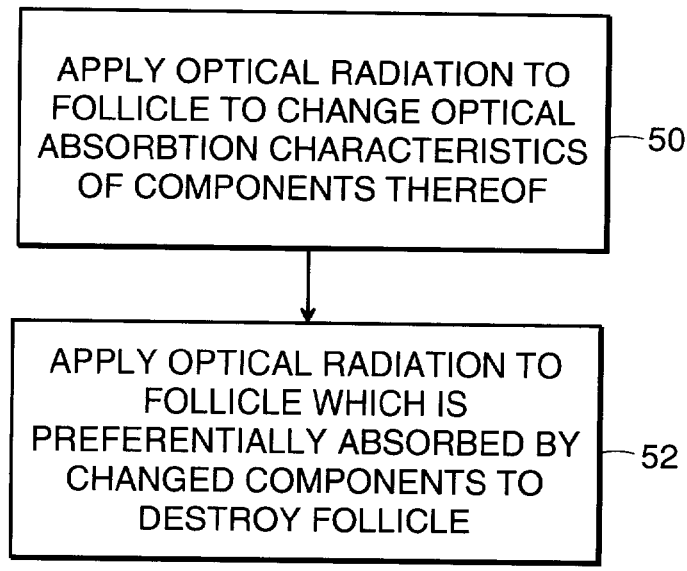
FIG. 2 is a schematic flow diagram of the basic concept of this invention.

FIG. 2 illustrates the general procedure for hair removal in accordance with the teachings of this invention. Referring to this Figure, during step 50, the first step in the operation, applicator 32 is positioned either over or in contact with the area of the patient's skin where epilation is to be performed, and controls 38 then operate S1 source 36A to apply optical radiation of a selected wavelength, energy and duration to follicle 10 so as to cause a change in color of the follicle, and in particular to change or enhance the optical absorption characteristics of at least some components thereof. While for purposes of illustration, applicator 32 is shown as overlying only a single follicle in FIG. 1, in a practical system, applicator 32 would overly an area of the patient's skin which may contain multiple follicles. One of the advantages of this invention is that, since it requires a far lower fluence, and at least for the radiation of step 50, can operate with only relatively low fluence radiation, the same power source can be utilized to cover a significantly larger area of the patient's skin, thus permitting the hair removal procedure to be performed in significantly less time. In particular, the speed at which the hair removal procedure can be performed is directly proportional to the power of the source 36 and inversely proportional to the fluence (i.e., V=P/F, where V is in cm$^2$/s, P is in watts and F is in J/cm$^2$). Thus, the decrease from the 30–40 J/cm$^2$ required in the prior art to destroy a hair follicle and achieve permanent hair removal to the 1–5 J/cm$^2$ fluence required in accordance with the teachings of this invention to achieve the same objective results in an approximately ten-fold reduction in the time required to perform at least substantially permanent hair removal. While this time advantage can be significantly mitigated by the need for multiple pulses, as will be discussed in greater detail in conjunction with FIG. 3, significant reductions in treatment time are still possible utilizing the teachings of this invention.

Head 32 may be designed to cover larger areas in at least two ways. One way is to use a head having an optical aperture for surface 34 with a generally circular area of the desired size, for example an optical aperture having a 12 mm diameter, or possibly even larger. A second way of accomplishing this objective is for the head to be elongated in the direction into the page. The latter design would be particularly advantageous where the control of fluence is achieved by moving head 32 over the treatment area at a controlled rate, while maintaining the source 36 continuously energized. Such a mode of operation is discussed in co-pending provisional application Ser. No. 60/046,542, filed May 15, 1997.

What is important during step 50 is that the optical absorption characteristics of components of the follicle be altered in a manner so as to render the follicle more susceptible to destruction by subsequently received radiation, without the radiation being high enough to endanger either the patient's epidermis or any other tissue surrounding the follicle in a significant way. As indicated earlier, this objective can generally be achieved with a pulse or other radiation signal applied to the area under treatment having a fluence in the one to of 5 J/cm$^2$ range.

Figure 3:
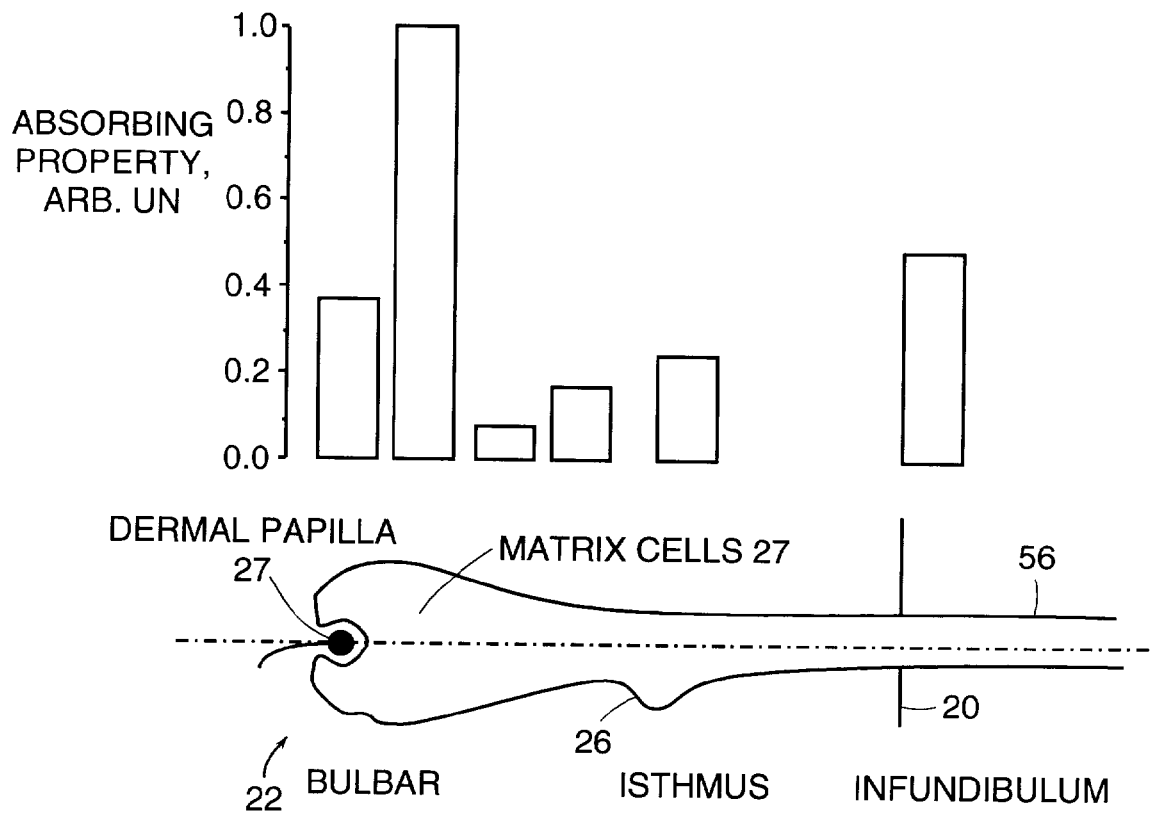
FIG. 3 is a diagram illustrating a hair follicle and the relative absorption of ruby laser radiation at selected points along such follicle.
Figure 4:
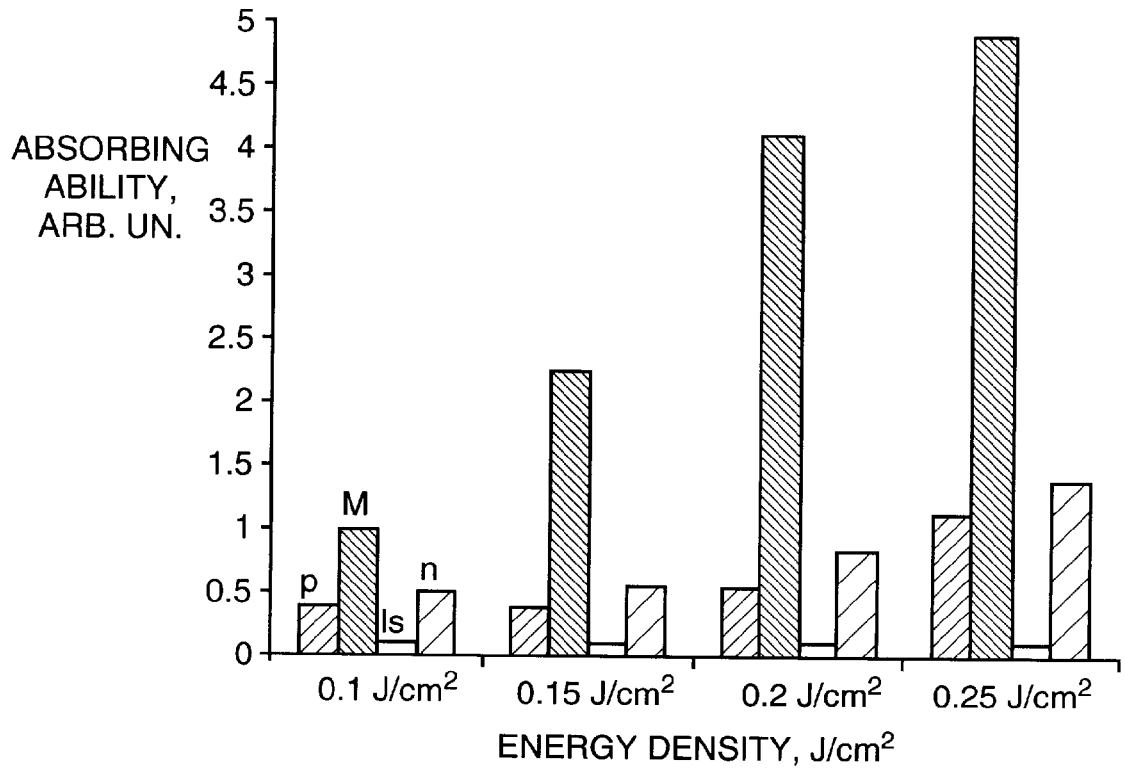
FIG. 4 is a chart indicating the relative absorption of ruby laser radiation at four of the points indicated in FIG. 3 for different energy densities at the bulb of the follicle.

While in the discussion above it is suggested that step 50 involves the application of only a single pulse or signal to the area under treatment, and this is true for some embodiments of the invention as discussed later, there are also embodiments of the invention where step 50 is accomplished by applying multiple pulses or signals to the follicle to alter the optical characteristics of increasing numbers of components (i.e., melanosomes, tissue, etc.) within the follicle. FIGS. 3 and 4 illustrate to some extent the mechanism which comes into play during step 50. An anegen stage hair shaft/follicle is shown as divided into three areas, the bulbar or bulb area 22, the isthmus or bulge area 24 and the infundibulum area 56 extending beyond the bulge to and beyond the skin surface. Since most of the melanosomes are in the matrix cell area of the hair shaft, and melanin in a hair shaft in fact originates in this area, from FIG. 3 it is seen that the absorption of light from a ruby laser at a wavelength of approximately 694 nm is greatest by a substantial amount in this area, the lower absorption around the papilla reflecting the fact that there are less matrix cells in this area than at the wider portion of the bulb. Absorption drops off beyond the matrix cells, reflecting a lower concentration of melanin in this area, increasing again in the bulge area, and then virtually disappearing until the area adjacent the D-E junction 20 where melanin is picked up from the junction.

FIG. 4 indicates the absorption at the four major absorption points in the follicle as a function of energy in J/cm$^2$ at the bulb, where the energy at the bulb is roughly $\frac{1}{3}$ to $\frac{1}{10}$th the incident energy at the skin surface. Thus, 0.2 J/cm$^2$ at the bulb would be equal to 0.6 to 2.0 J/cm$^2$ at the skin surface, depending on such factors as pressure applied by the applicator to the skin, the parameters of the patient's skin, the depth of the bulb in the dermis, etc. From FIG. 4 it is seen that the absorption increases more sharply with increasing energy in the areas containing large amounts of melanin, while increasing barely at all for areas having low melanin concentration. This suggests that higher energy radiation can be used for darkened areas with high melanin concentration and areas adjacent thereto without significant damage to areas having low melanin concentration.

Whether step 50 involves a single pulse or multiple pulses, once this step has been completed, the operation proceeds to step 52 during which optical radiation is applied to the follicle, which radiation is of a wavelength preferentially absorbed by the components having the changed optical characteristics. This preferential absorption may be accomplished by providing radiation during step 52 which is absorbed more readily by the altered components then by components such as blood or melanin contained outside the follicle, and in particular in the epidermis, which it is desired to protect. Alternatively, a broad-band radiation can be used during this step, where the components to be destroyed have been altered to a state which absorbs across a broad band, while tissue, melanosomes, etc. outside the follicle which are to be protected absorb only across a narrow band. Therefore, most of the energy from the broad band source is absorbed by the changed components, while very little energy from this source is absorbed by the components to be protected. For at least some embodiments of the invention, this preferential absorption permits larger energy to be used during step 52 than during step 50, thereby facilitating permanent hair removal without significant damage to the epidermis or other surrounding tissue. As will be discussed later, step 52 may also be a single pulse, multiple pulses, a continuous wave signal which is successively supplied to areas of the patient's skin or, for at least one embodiment of the invention, another portion of the same pulse used in performing step 50. Further, since carbon is not metabolized into the skin, step 52 does not need to be performed immediately after step 50, but can be performed hours, or even a day or more later. If there has been sufficient darkening of follicle components, step 52 could, in some cases, be performed over time by sunlight or other suitable ambient light. Step 52 thus takes advantage of the changed optical characteristics of the follicle components to destroy the follicle, and in some instances, some tissue immediately surrounding the follicle so as to cause permanent or near permanent hair removal. Even where permanent or near permanent hair removal is not achieved, the state of the hair can be changed from the terminal state where the hairs are thick and, for most individuals, of a dark color, to the vellus state where the hairs are much like a babies hair, being thin and substantially colorless. In many instances, this transition in the hair is sufficient to meet the requirements of the patient in certain areas of the body.

Figure 5:
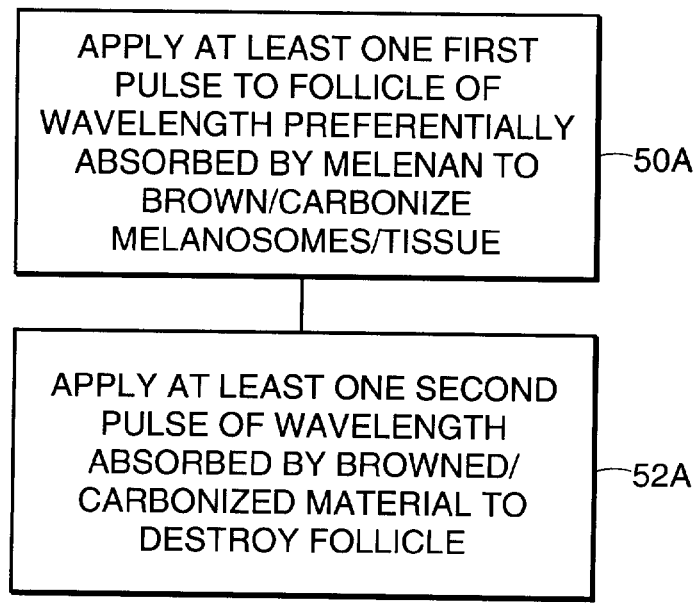
FIG. 5 is a schematic flow diagram of one embodiment for the technique of this invention.

The method of FIG. 2 may be implemented in a variety of ways, one of which is illustrated in FIG. 5. For this embodiment of the invention, step 50 is performed by energizing source 36A which is a laser or other light source operating at a wavelength which is preferentially absorbed by melanin. While melanin absorbs wavelengths in the range of 600–1100 nm, preferential absorption by melanin is generally in a wavelength band of approximately 650–800 nm. A ruby laser operating at 694 nm is one example of a first source 36A suitable for preferentially targeting melanin. An alexandrite laser operating at 750–790 nm is another example of a suitable source. However, source 36A may also be various diode lasers or even a wide band source such as various lamps which are preferably filtered to provide most of their output within the desired band.

As indicated previously, melanin is concentrated in follicle 12 within a bulb portion or region 22, although some melanin appears in other portions of the follicle. Depending on the patient, there also may be significant melanin at DE junction 20, although this melanin is not as concentrated as that at bulb 22. The pulse supplied during step 50A is sufficient so as to at least brown and to preferably carbonize or blacken at least some of the melanosomes in bulb 22. With low energy, the lower concentration of melanosomes at the junction 20 may prevent significant browning or carbonization of the melanosomes in this area. If necessary, such color change at the DE junction may be further inhibited by providing some cooling at the skin surface in a number of ways known in the art.

Figure 8A:
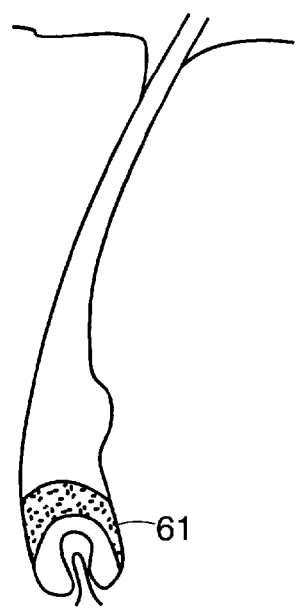
FIGS. 8a–8d illustrates the condition of the follicle before radiation, and after 1, 2, and 3 radiation pulses, respectively for an illustrative implementation of the FIG. 7 embodiment.
Figure 8B:
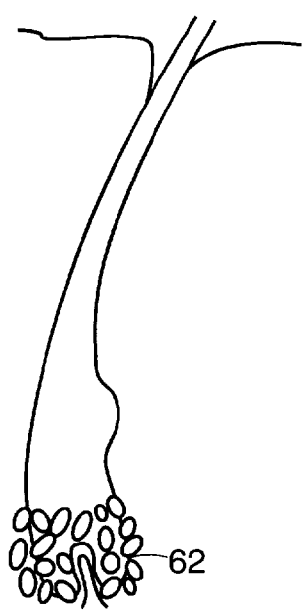
Figure 8C:
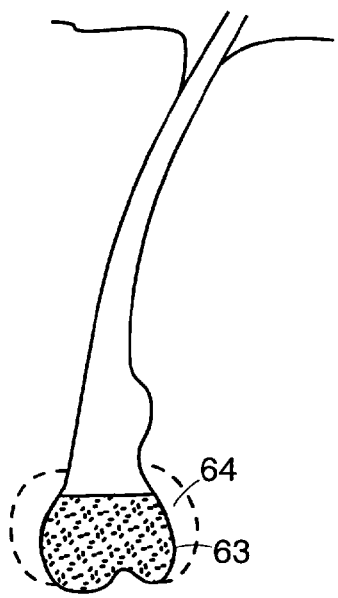
Figure 8D:
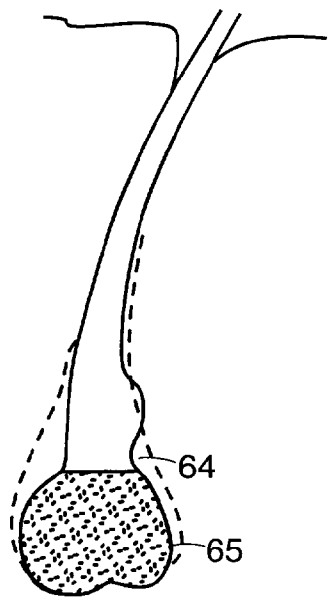

It has been found that the heating of the melanosomes, particularly in bulb 22, results in the evaporation of water vapor in surrounding tissues, resulting in the formation of bubbles around the darkened melanosomes, and in particular, around the bulb itself (See FIG. 8*b*). Since there is a greater concentration of water in tissue then there is in the bulb, and in particular in matrix 27 thereof, less of the energy received at these components is required to evaporate the water and more can therefore be utilized for browning. The bubbles formed by evaporation provide some insulation, holding heat in the bulb to accelerate the carbonization on subsequent pulses.

While only a single low energy pulse may be used for step 50A, it is generally preferable to provide two or more such pulses at lower energy for a number of reasons. First, this permits either a lower energy source to be used, or a larger area to be covered from a given source. Second, the browning/carbonization or darkening of the melanosomes increases generally exponentially for each successive pulse. One reason for this is that, as the melanosomes and the surrounding tissue darken, they become better absorbers of optical radiation, and are therefore capable of generating more heat to darken an increasing number or percentage of the melanosomes and of the surrounding tissue in the follicle and tissue immediately adjacent thereto, and more particularly the bulb area 22. Further, initial pulses evaporate water vapor surrounding the melanosomes, meaning that less energy must be devoted to this function in subsequent pulses, permitting these pulses to be more effective in causing browning or carbonization of the melanosomes and of the tissues surrounding the melanosomes which are heated by the melanosomes.

Once step 50A has been completed to darken a sufficient percentage of the melanosomes and tissue in the follicle area, the operation proceeds to step 52A during which at least one pulse is applied which is of a wavelength preferentially absorbed by the browned/carbonized melanosomes/tissue and of energy and duration to cause substantial destruction of the follicle. While step 52A would normally be accomplished with a single pulse, this is not a limitation on the process, and two or more pulses could be utilized. The pulse used during step 52A is preferably from a source 36B which is at a wavelength different from that used during step 50A. In particular, source 36B could be an Na:Yag laser operating at a wavelength of 1060 nm, which wavelength is not significantly absorbed by either melanin or blood, but is absorbed by a brown or black body such as carbonized melanosomes or tissue. Alternatively, source 36B could be a broad-band source such as in incandescent lamp, mercury lamp, halogen lamp, fluorescent lamp, flash lamp, or the like. While some portions of the radiation from these sources will be absorbed by melanin or blood, the total absorption will not be great and would be far less than the radiation absorbed by the blackened melanosomes/tissue which absorb across the entire spectrum. Therefore, a pulse output from source 36B may be of much higher energy and for a much longer duration without causing damage to the epidermis or surrounding tissue, concentrating its damage in the darkened portions of the follicle. Fortuitously, such darkened portions are the portion of the follicle which need to be destroyed in order to achieve permanent or near permanent hair removal. Further, while the lasers required to achieve the spectial bands attacking melanosomes are relatively expensive, particularly if high powered lasers are required, the source 36B, whether an Na: Yag laser or some type of lamp, are relatively inexpensive, even at relatively high energy. The technique of FIG. 5 thus results in permanent or near permanent hair removal at lower costs with less danger to the patient and more quickly then can be achieved using most existing techniques.

Figure 6:
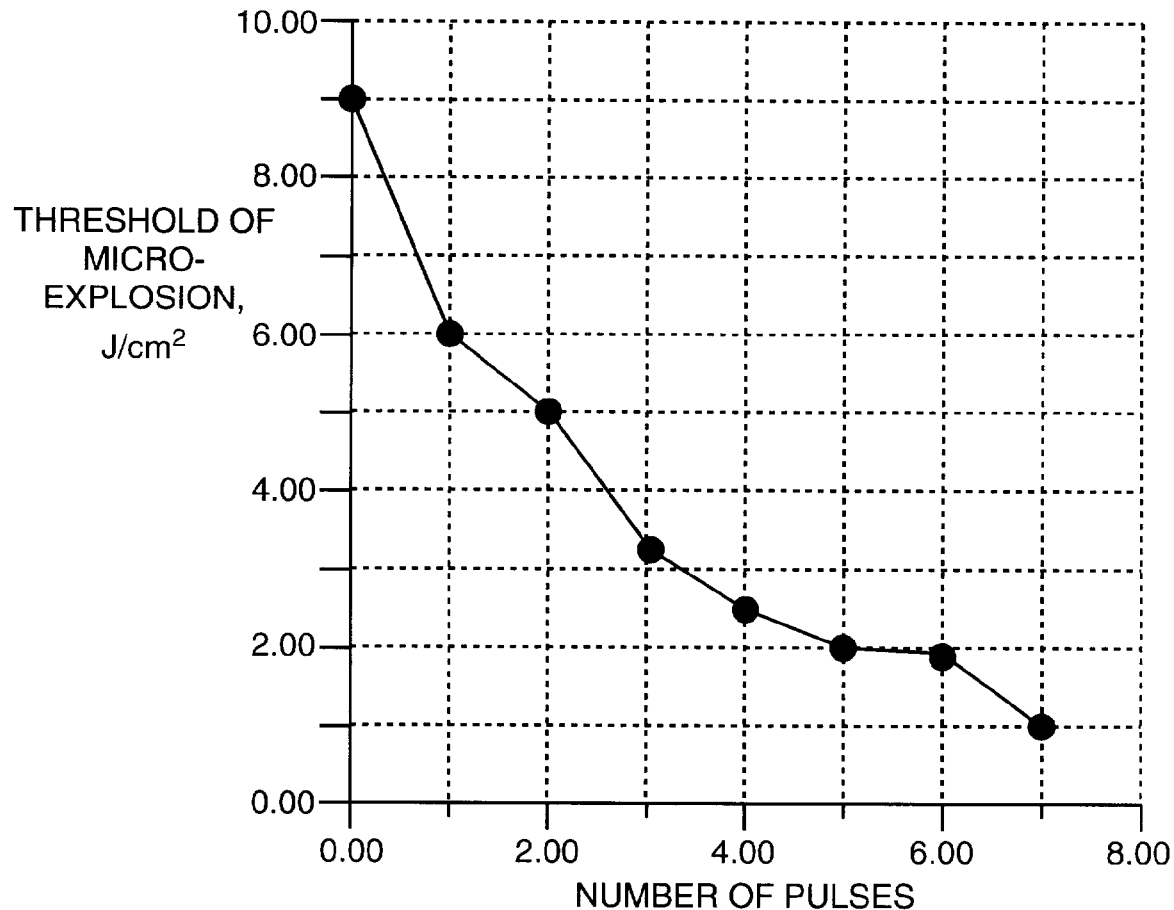
FIG. 6 is a chart illustrating the energy required for a second pulse from a Na:YAG laser in order to cause explosion of the bulb as a function of the number of ruby laser pulses.

FIG. 6 is a chart illustrating the energy in $J/cm^2$ required from a Nd:Yag laser producing an 0.5 ms pulse at 1060 nm in order to explode bulb 22, which generally results in destruction of the follicle, as a function of the number of ruby laser pulses, each of one millisecond duration and energy previously applied to the follicle during step 58. It is seen that the energy for the Na:YAG laser drops off from approximately 9 J/cm² where no step 50A pulses are applied, to 2 J/cm² for five step 50A pulses and only 1 J/cm² for nine step 50A pulses. Similar results can be achieved with other step 50A and step 50B radiation sources and parameters.

Figure 7:
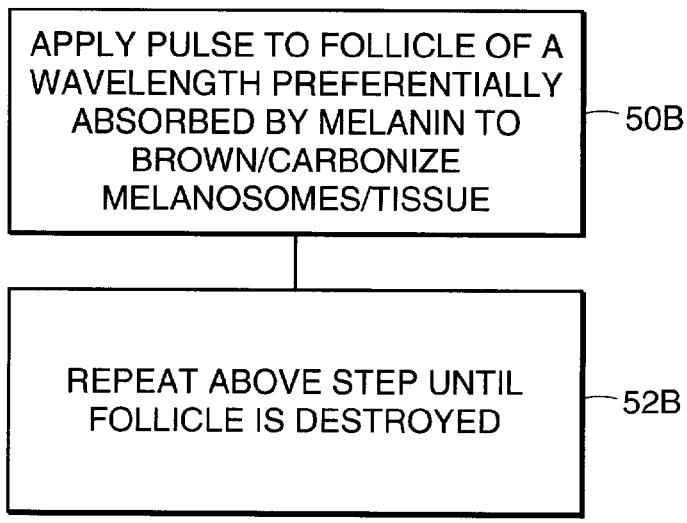
FIG. 7 is a schematic flow diagram of a second embodiment implementing the teachings of this invention.

FIGS. 7 and 8 show an alternative technique utilized for practicing the teachings of this invention. For the embodiment of FIGS. 7 and 8, step 50B involves applying a pulse to the follicle of a wavelength preferentially absorbed by melanin to brown or carbonize the melanosomes and tissue much as for step 50A of FIG. 5. For this embodiment of the invention, the fluence of the pulse may be on the higher end of the pulses used for this function, for example, 3–5 J/Cm². FIG. 8a shows the follicle before radiation, with melanosomes 61 in matrix area 27. The first pulse browns and/or carbonizes some of the melanosomes in bulb 22 and perhaps other areas of the follicle, and may also result in some browning or carbonization of surrounding tissue, but also results in the evaporation of water from such surrounding tissue, resulting in bubbles 62 being formed around the melanosomes as shown in FIG. 8b. As previously indicated, bubbles 62 form an insulating cover around bulb 22, holding heat in the bulb to accelerate the darkening process. Step 52B then involves repeating step 50B as many times as is required to destroy the follicle. As is seen in FIGS. 8c and 8d, each subsequent pulse results in the darkening, either browning or carbonization, of more melanosomes, and thus in an increased concentration of carbonized or browned melanosomes in bulb 22 (63 illustrating the carbonized area), bulge 24 and other areas of the follicle. The heating of the bulb also results in browned/carbonized tissue 64 surrounding the bulb, and ultimately other portions. Since, as previously indicated, each successive pulse needs to expend less energy in evaporating water from tissue, and since each successive pulse is absorbed more by dark or black bodies, such as carbonized melanosomes/tissue or browned melanosomes/tissue, which are far better absorbers of such radiation and, therefore, provide more heat in the follicle for a given quantity of applied radiation, the quantity of melanosomes/tissue which are carbonized or otherwise darkened increases substantially exponentially for successive pulses. With an exponential increase in tissue destruction in the follicle, after a certain number of pulses, which will vary with factors such as the colorization of the patient (i.e, the quantity of melanosomes in the patient's follicle and hair shaft) and the applied fluence, all or substantially all of the tissue in the follicle will be destroyed, resulting in the destruction of the follicle, and in permanent or substantially permanent hair removal. In particular, a swelling of bulb area 22 may occur; as shown in area 65 (FIG. 8d), which may result in the explosion of this area. Typically, approximately 5–10 pulses in the 0.5–5 J/cm² fluence range would be required to achieve this result.

Figure 9:
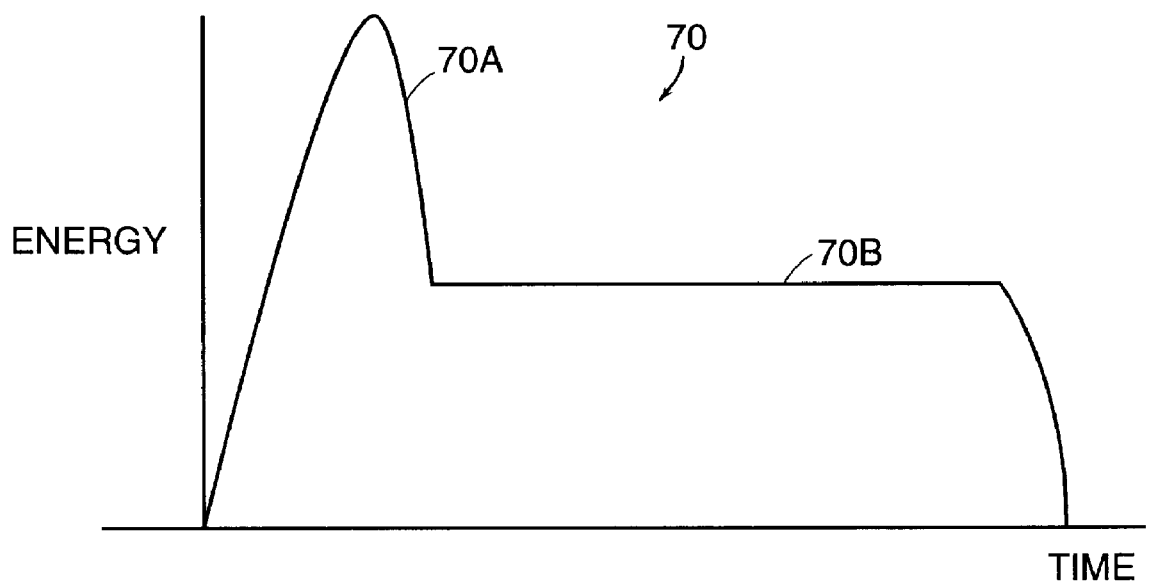
FIG. 9 is a pulse diagram illustrating a pulse suitable for use in practicing the teachings of this invention in accordance with a third embodiment thereof.

FIG. 9 illustrates a pulse 70 which may be utilized for still another embodiment of the invention where in a single pulse from for example source 36A is utilized. Pulse 70 has an initial spiked portion 70A which performs the function of step 50 in much the same way this function is performed by an initial pulse for step 50A or 50B. The second portion of the pulse, 70B, performs the function of step 52, this portion of the pulse being of much longer duration and at low power density to minimize epidermal or other significant tissue damage outside of the follicle. Spike 70A may, for example, be at 1.0 J/cm² to 10 J/cm² with a duration of 0.1 ms to 5 ms, and pulse portion 70B might, for example, be at 5 J/cm²–100 J/cm² with a time duration of approximately five ms to one second.

While three specific implementations for the technique of FIG. 2 have been described above, it is apparent that these embodiments are by way of example only and that other techniques are available for changing or darkening components of a hair follicle so as to enhance their optical absorption characteristics, and to then provide optical radiation to the follicle which is absorbed by such altered components in a manner so as to destroy the follicle. The hardware shown in FIG. 1 is also for purposes of illustration only, and a variety of hardware configurations, either known in the art of otherwise, might be utilized in practicing the teachings of the invention. The specific components used are not critical so long as the desired results are obtained. Thus, while the invention has been particularly shown and described above with reference to preferred embodiments, the foregoing and other changes in form and detail may be made therein by one skilled in the art while still remaining within the spirit and scope of the invention.

What is claimed is:

1. A method for the removal of and for at least inhibiting the regrowth of a patient's hair growing from a hair follicle, the method comprising the steps of:

(a) applying at least one optical radiation pulse to the follicle, each said pulse being of an energy, duration and wavelength to enhance the optical absorption characteristics of at least one of melanosomes in the follicle, tissue heated by adjacent melanosomes or tissue whose optical absorption characteristics were previously enhanced and without appreciably damaging skin outside the follicle; and (b) applying optical radiation to the follicle of a wavelength which is more readily absorbed by said components of the follicle having optical absorption characteristics enhanced during step (a) then by unenhanced components of the follicle and of an energy and duration to heat such enhanced components sufficiently to substantially destroy the follicle.

2. A method as claimed in claim 1 wherein, during step (a), melanosomes in the follicle are heated sufficiently to at least partially darken such melanosomes by browning/carbonization.

3. A method as claimed in claim 2 wherein tissue surrounding said melanosomes is also darkened.

4. A method as claimed in claim 2 wherein the optical radiation applied during step (a) is of a wavelength preferentially absorbed by melanosomes.

5. A method as claimed in claim 2 wherein the optical radiation applied during step (b) is of a wavelength absorbed by browned/carbonization components, but not preferentially absorbed by melanosomes.

6. A method as claimed in claim 5 wherein the optical radiation applied during step (b) is at approximately 1060 nm.

7. A method as claimed in claim 2 wherein the optical radiation applied during step (b) is from a wideband lamp.

8. A method as claimed in claim 2 wherein the optical radiation applied during step (a) is in the form of a pulse having an energy sufficient to darken melanosomes in said follicle, but not sufficient to substantially darken epidermal melanosomes.

9. A method as claimed in claim 1 wherein the optical radiation applied during step (a) is in the form of a single pulse.

10. A method as claimed in claim 1 wherein the optical radiation applied during step (a) is in the form of a plurality of pulses, each successive pulse enhancing the optical absorption characteristics of additional components of the follicle.

11. A method as claimed in claim 10 wherein optical radiation pulses applied during step (a) heat and darken by browning/carbonization components in said follicle, darkened components formed during one said pulse absorbing optical radiation of each said successive pulse to heat and darken said additional components of the follicle.

12. A method as claimed in claim 11 wherein successive pulses are applied during step (a) to darken sufficient components in the follicle so that the next said successive pulse functions as step (b) optical radiation.

13. A method as claimed in claim 1 wherein the energy for the optical radiation of step (b) is significantly greater than the energy for the optical radiation of step (a).

14. A method as claimed in claim 1 wherein optical radiation for step (a) and step (b) are at different wavelengths.

15. A method as claimed in claim 1 wherein optical radiation for step (a) and step (b) are at the same wavelength.

16. A method as claimed in claim 15 wherein optical radiation for step (a) and step (b) are from the same pulse.

17. A method as claimed in claim 16 wherein said pulse has a narrow spike as the step (a) optical radiation and an extended plateau as the step (b) optical radiation.

18. Apparatus for epilation of hair in a treatment area of a patient's skin, each of said hairs growing from a hair follicle, including:
  a source of radiation having a wavelength in the 600 to 1100 nm range;
  an applicator for applying radiation from said source to said treatment area;
  first controls for operating said source to apply a pulse of the radiation from said source through said applicator to said treatment area, which pulse is of a wavelength, duration and energy to cause heating of melanosomes in a said follicle sufficient to darken the melanosomes and tissue surrounding such melanosomes by browning/carbonization, but not sufficient to destroy the follicle; and
  second controls operative to apply successive said pulses of radiation to said area, each said successive pulse heating both the melanosomes and darkened tissue sufficiently to result in further tissue darkening in the follicle, said second controls applying a sufficient number of said pulses to said treatment area to result in the destruction of the follicle.

19. Apparatus as claimed in claim 18 wherein said source is a continuous wave source, and wherein said applicator is passed over said treatment area a plurality of times, each pass of the applicator over the area resulting in a said pulse being applied to the area.

20. Apparatus as claimed in claim 19 wherein said hairs to be epilated are in a plurality of adjacent areas, and wherein said applicator makes a plurality of passes over said areas, the areas being passed over in succession during each pass.

21. Apparatus as claimed in claim 18 wherein said source is a pulsed source, said source being pulsed to apply a radiation pulse to a said area when the applicator is over the area.

22. Apparatus for epilation of hair in a treatment area of a patient's skin, each of said hairs growing from a hair follicle comprising:
  a source of radiation having a wavelength in the 600 to 1100 nm range;
  an applicator for applying radiation from said source to said treatment area;
  first controls for applying at least one first pulse of optical radiation from said source through said applicator to said treatment area, each said first pulse being of an energy, wavelength and duration to enhance the optical absorption characteristics of at least one of melanosomes in the follicle, tissue heated by adjacent melanosomes or tissue whose optical absorption characteristics were previously enhanced and a hair shaft in the follicle (components) without appreciably damaging skin outside the follicle; and
  second controls for subsequently applying at least one second pulse of optical radiation to the follicle of a wavelength which is more readily absorbed by said components having enhanced optical absorption characteristics then by unenhanced components and of an energy and duration to heat such enhanced components sufficiently to substantially destroy the follicle.

23. Apparatus as claimed in claim 22 wherein both said first pulses and said second pulses are from the same source of radiation.

24. Apparatus as claimed in claim 22 including a second source of radiation at a wavelength more readily absorbed by said components of the follicle having enhanced optical absorption characteristics then by unenhanced components, wherein said first pulses are from said source, and wherein said second pulses are from said second source.

* * * * *